(12) United States Patent
Geiger

(10) Patent No.: US 7,887,503 B2
(45) Date of Patent: Feb. 15, 2011

(54) METHOD AND APPARATUS FOR REMOVING HARMFUL PROTEINS FROM A MAMMALIAN'S VENTRICULAR CEREBROSPINAL FLUID

(76) Inventor: Mark Geiger, 4 Via Vetti, Laguna Niguel, CA (US) 92677

( * ) Notice: Subject to any disclaimer, the term of this patent is extended or adjusted under 35 U.S.C. 154(b) by 592 days.

(21) Appl. No.: 11/986,299

(22) Filed: Nov. 20, 2007

(65) Prior Publication Data
US 2009/0131850 A1    May 21, 2009

(51) Int. Cl.
A61M 5/00   (2006.01)
A61M 37/00  (2006.01)
(52) U.S. Cl. .......................................... 604/9; 604/6.09
(58) Field of Classification Search .................. 604/8, 604/9, 10, 6.09, 6.1; 210/645, 500.21
See application file for complete search history.

(56) References Cited

U.S. PATENT DOCUMENTS

| | | | | |
|---|---|---|---|---|
| 4,446,155 A | * | 5/1984 | Osterholm | 424/780 |
| 4,904,237 A | * | 2/1990 | Janese | 604/28 |
| 4,995,401 A | * | 2/1991 | Bunegin et al. | 600/561 |
| 5,385,541 A | * | 1/1995 | Kirsch et al. | 604/8 |
| 5,772,625 A | * | 6/1998 | Krueger et al. | 604/9 |
| 2006/0020239 A1 | * | 1/2006 | Geiger et al. | 604/9 |
| 2008/0114337 A1 | * | 5/2008 | Ahmed | 604/541 |

OTHER PUBLICATIONS

Epstein ("Cerebrospinal Fluid Production: Stimulation by Cholera Toxin", Science Magazin, vol. 196, May 1977).*

* cited by examiner

Primary Examiner—Leslie R Deak
(74) Attorney, Agent, or Firm—Moser Law Group

(57) ABSTRACT

A method and apparatus for removing harmful organic anions and proteins from a mammalian's ventricular cerebrospinal fluid in the treatment of brain disorders. One embodiment comprises using an implanted pump and filter system in conjunction with a drug or enzyme to clean and filter a patient's cerebrospinal fluid.

7 Claims, 5 Drawing Sheets

METHOD AND APPARATUS FOR REMOVING HARMFUL PROTEINS FROM A MAMMALIAN'S VENTRICULAR CEREBROSPINAL FLUID

BACKGROUND OF THE INVENTION

1. Field of the Invention

Embodiments of the present invention generally relate to therapeutic mechanisms for treating brain disorders, and more particularly, to a method and apparatus for removing harmful organic anions and proteins from a mammalian's ventricular cerebrospinal fluid in the treatment of brain disorders.

2. Description of the Related Art

In advanced aging and with brain disorders such as Alzheimer's Disease, there are many degenerative changes in the cranial compartment, particularly in the choroid plexus. The choroid plexus is the area of the brain that is responsible for the production of cerebrospinal fluid (CSF). Some of the degenerative changes have adverse effects on the normal removal of organic anions and proteins from ventricular cerebrospinal fluid ("Volume Transmission of CSF: Complications in Aging and AD, Johansson et. al., Brown Medical School, CSF Research 2004). Cerebrospinal fluid is a clear bodily fluid that maintains, cradles, cushions and bathes the central nervous system. Cerebrospinal fluid occupies the spine's sub-arachnoid space and the ventricular system around and inside the brain.

In addition, the CSF system maintains a delicate balance between production and absorption of cerebrospinal fluid. This is especially true as the brain loses its elasticity in the aging process. Some clinicians have reported that there is a relationship between Alzheimer's disease (AD) and Normal Pressure Hydrocephalus (NPH). Thus, accessing the CSF system in the cranial or spinal subarachnoid space to administer therapeutic treatment for brain disorders may disturb the system's delicate balance leading to complications (e.g., CSF leak or NPH). Such complications may necessitate some level of temporary or permanent CSF diversion. Further, experts such as Michael Williams, MD of John Hopkins University have suggested that patients experiencing symptoms of AD and NPH may not have one or the other, but instead have a certain degree of both diseases.

However, such access of the CSF system may be necessary because of the Blood-Brain-Barrier. The Blood-Brain-Barrier is the body's natural central nervous system defense mechanism. The Blood-Brain-Barrier is very effective in restricting the movement of certain molecules to the brain. Therefore, infections of the brain are quite rare. Ironically, the same effective protection makes the treatment of brain infections or diseases that do occur very difficult. That is, the Blood-Brain-Barrier prevents therapeutic drugs that may be introduced into the blood stream or taken orally from reaching the brain in the same manner in which harmful substances or infections are prevented from reaching the brain.

Accordingly, there exists a need for a method of removing harmful organic anions and proteins from a mammalian's ventricular cerebrospinal fluid without upsetting the delicate balance of cerebrospinal fluid production and absorption in the CSF system.

SUMMARY OF THE INVENTION

The present invention generally relates to a method and apparatus for removing harmful organic anions and proteins from a mammalian's ventricular cerebrospinal fluid in the treatment of brain disorders like Alzheimer's Disease.

One embodiment of the present invention is a method for removing harmful organic anions and proteins from a mammalian's ventricular cerebrospinal fluid comprising implanting a combined reservoir, pump and filter system to filter and clean cerebrospinal fluid. The pump and filter system includes a power supply compartment, an access port for injecting a medicinal dose and for removing filtered material, a drug and filter reservoir and, and a pump, wherein the access port, the drug reservoir and the pump and filter system are in fluid communication. The method further comprises implanting a dual lumen catheter in fluid contact with the pump and filter system and in fluid contact with the spine's sub-arachnoid space. Further still, the method comprises supplying a medicinal dose into the drug and filter reservoir via the access port, extracting cerebrospinal fluid from the sub-arachnoid space into the drug reservoir via a first lumen of the catheter, delivering the cerebrospinal fluid through the filter back into the sub-arachnoid space via a second lumen of the catheter, removing filtered material from the pump and filter system via the access port, and supplying another medicinal dose into the drug and filter reservoir when a another medicinal dose is required.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

While the invention is described herein by way of example using several embodiments and illustrative drawings, those skilled in the art will recognize that the invention is not limited to the embodiments of drawing or drawings described. It should be understood that the drawings and detailed description thereto are not intended to limit the invention to the particular form disclosed, but on the contrary, the invention is to cover all modification, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must).

Similarly, the words "include," "including," and "includes" mean including, but not limited to. Further the word "a" is use to mean at least one.

DETAILED DESCRIPTION

Figure 1:
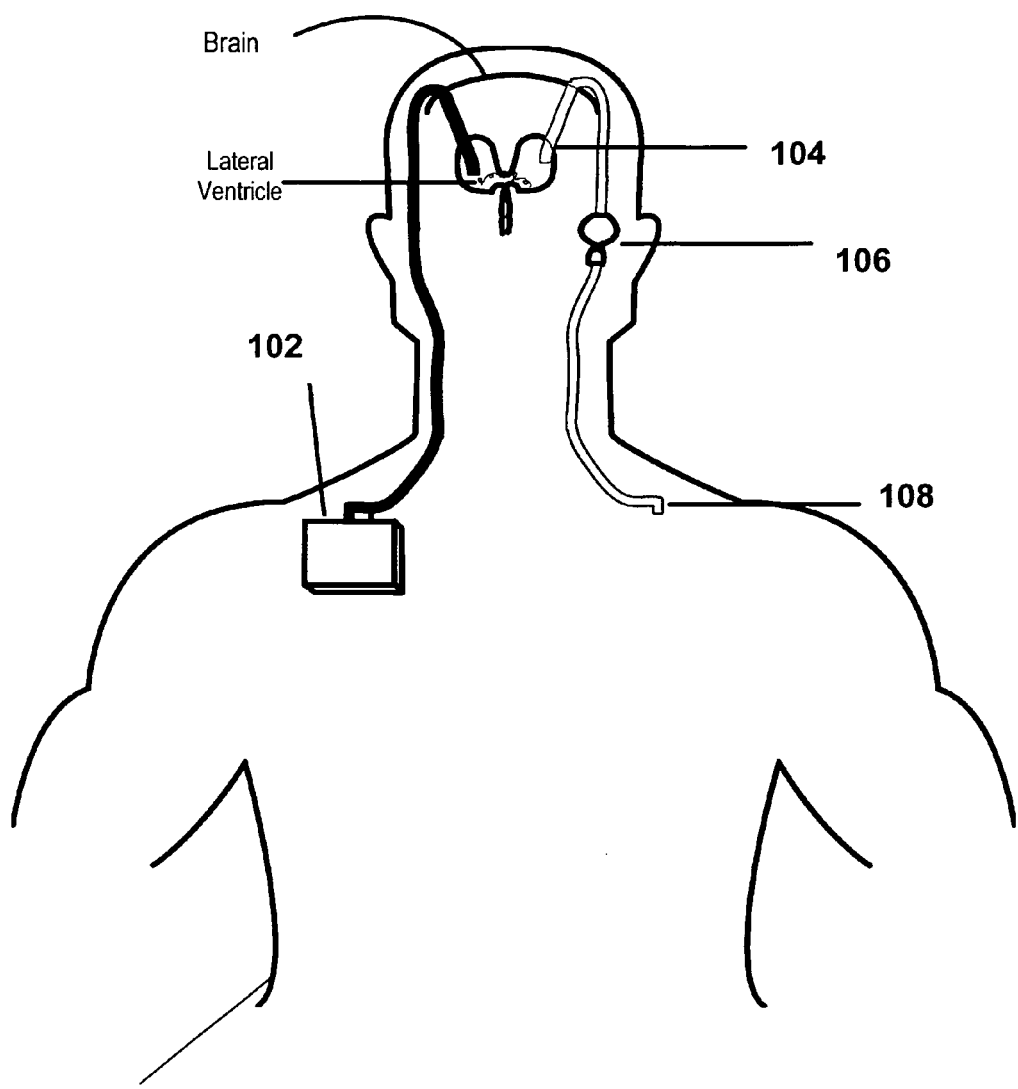
FIG. 1 is a drawing of a system for stimulating increased cerebrospinal fluid production, which depicts certain aspects of various embodiments of the present invention.

FIG. 1 is a drawing of a system for stimulating increased cerebrospinal fluid production, which depicts certain aspects of various embodiments of the present invention. As shown, neuro-stimulator 102 is implanted in a patient. The stimulator is connected to be in neuro-contact with the choroid plexus of the patient's brain. The choroid plexus is the section of the brain responsible for the production of cerebrospinal fluid. The neuro-stimulator may be of the type used in deep brain stimulation for the treatment of Parkinson's disease and essential tremor. Increased production of CSF may restore the normal removal of organic anions and proteins.

One end of ventricular shunt 104 is in fluid contact with the lateral ventricle of the patient's brain. The other end of ventricular shunt 104 is in fluid contact with flow control valve 106. Flow control valve 106 is also in fluid contact with catheter 108. Therefore, cerebrospinal fluid may be communicated from the lateral ventricle of the patient's brain to a chosen location in the patient's body to be re-absorbed.

According to one embodiment of the present invention, a cerebrospinal fluid shunt (e.g., ventricular shunt 104 with flow control valve 106) may be used in conjunction with a neuro-stimulator. The CSF shunt would be used to move cerebrospinal fluid from the lateral ventricle of the brain to another location (e.g., peritoneal cavity, right atrium of the heart, etc.) in the patient's body for re-absorption.

Figure 2:
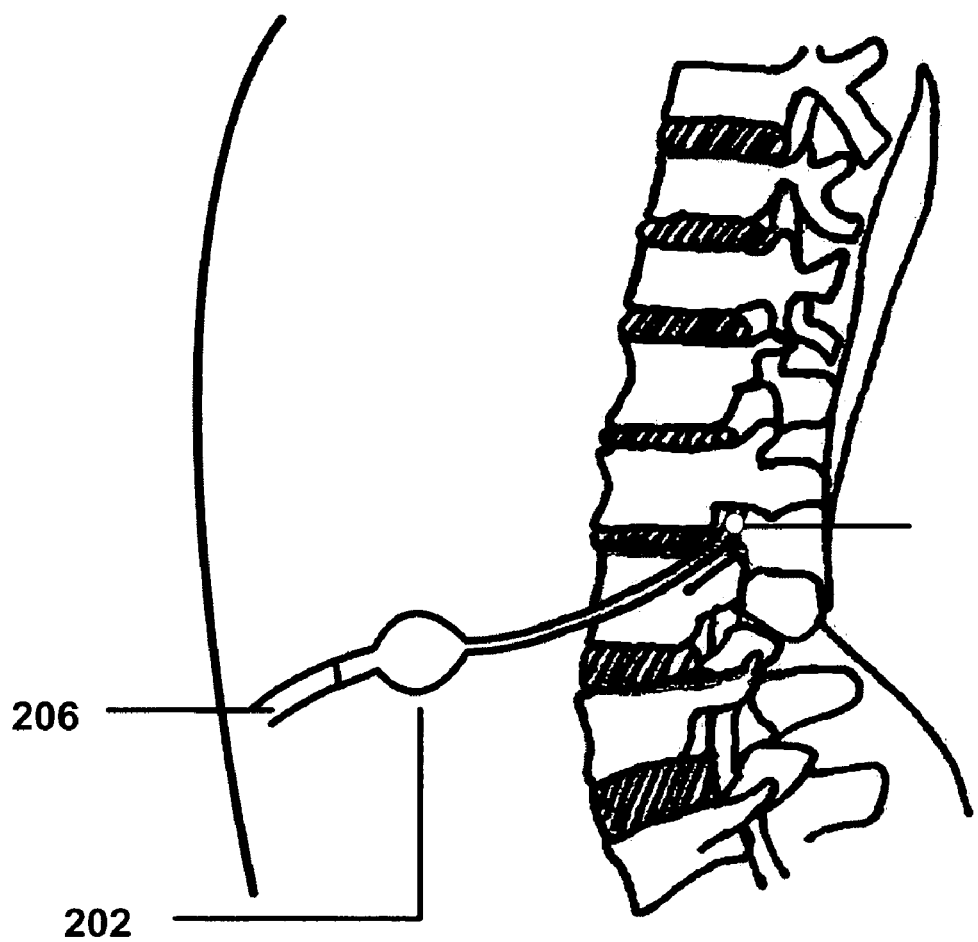
FIG. 2 is a drawing of a cerebrospinal fluid shunt which depicts certain aspects of various embodiments of the present invention.

Alternately, as depicted in FIG. 2, a lumbar cerebrospinal fluid shunt in fluid contact with the spinal subarachnoid space (e.g., lumbar CSF shunt 206 with flow control valve 202) may be utilized in conjunction with a neuro-stimulator (e.g., neuro-stimulator 102). In this embodiment, cerebrospinal fluid would be moved from the spinal subarachnoid space, instead of the lateral ventricle, to another location in the patient's body for re-absorption.

Figure 3:
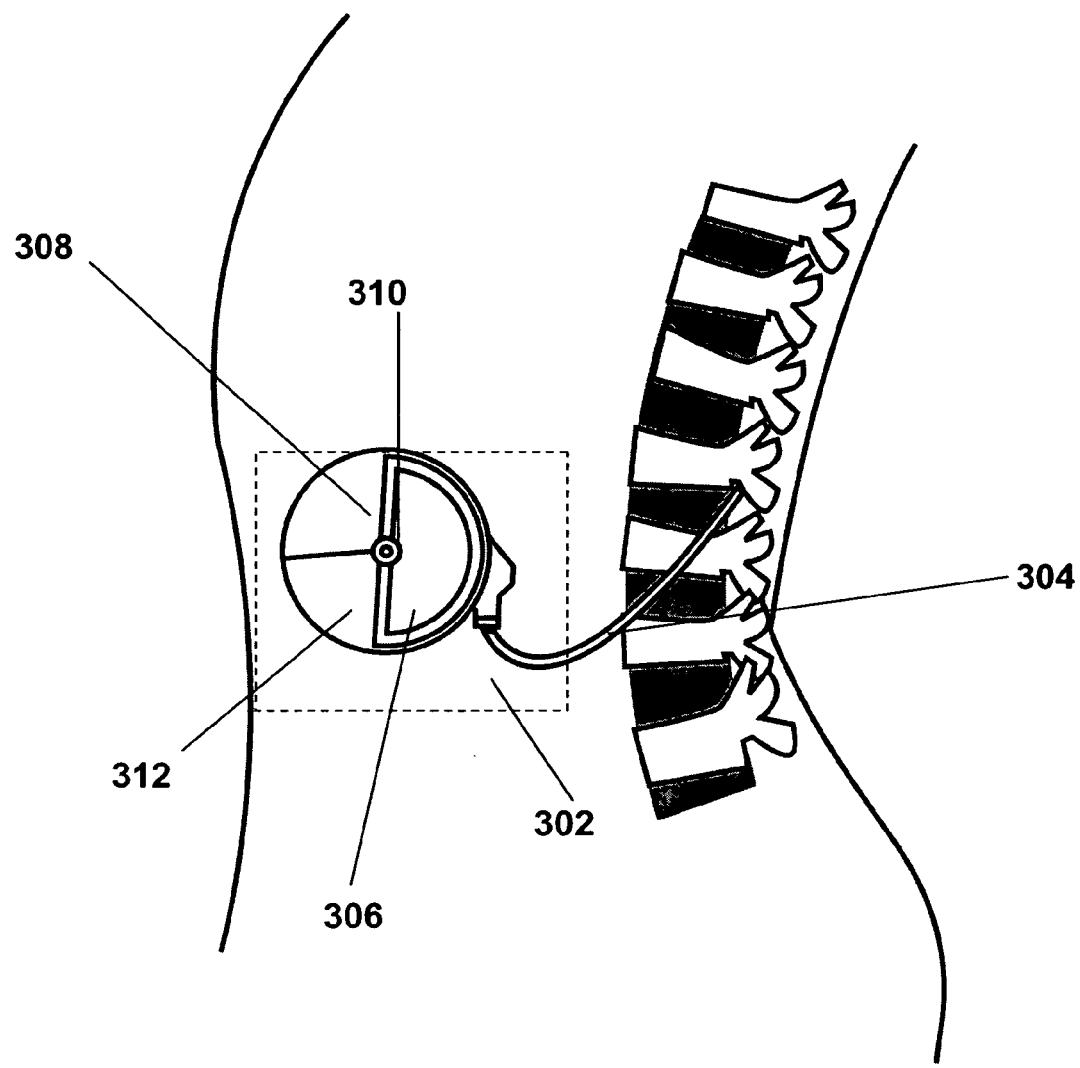
FIG. 3 is a drawing of a pump and filter for filtering cerebrospinal fluid, which depicts certain aspects of various embodiments of the present invention.

In accordance with various other embodiments of the present invention, a pump and filter system may be employed in removing harmful organic anions and proteins from a mammalian's ventricular cerebrospinal fluid. Such a system is depicted in FIG. 3. As shown, pump and filter system 302 comprises a dual lumen catheter 304 in fluid contact with drug and filter reservoir 306. Dual lumen catheter 304 is also in fluid contact with the spinal subarachnoid space of a patient. The pump and filter system further comprises a power supply 308, a drug port 310, and a pump 312. The drug and filter reservoir, drug port, and the pump are in fluid communication with each other. Therefore, the pump and filter system is in fluid communication with the spinal subarachnoid space of the patient.

According to at least one embodiment of the present invention, cerebrospinal fluid is pulled from the spinal subarachnoid space via a first lumen or catheter (e.g., the first lumen of dual lumen 304) of a pump and filter system (e.g., pump and filter system 302) into a drug and filter reservoir containing a drug (e.g., NeuroChems's Alzhemed™, reported in "7 ways to Save a Brain", Newsweek Special Issue, 2005) that attracts harmful proteins like A-beta and Tau. However instead of a drug, the drug and filter reservoir may contain an enzyme capable of digesting beta-amyloid (Purdue findings reveal possible Alzheimer's link to brain organ, Purdue University news, Mar. 21, 2006). After a therapeutically sufficient period of time for the medicinal dose to take effect has elapsed, cerebrospinal fluid is returned back to the spinal subarachnoid space via a second lumen or catheter (e.g., the second lumen of dual lumen 304) to be re-absorbed by the body. The pump and filter system may include an access port (e.g., drug port 310) that could be used to add the enzyme or drug, or to remove substances filtered from the cerebrospinal fluid. Additionally, the pump may also be non-invasively programmed to control flow rate, filtration rate, or other operational parameters of the pump and filter system.

It should be noted that the filter used in the pump and filter system is capable of retaining the drugs or enzymes within the drug and filter reservoir while permitting cerebrospinal fluid to pass through. That is, cerebrospinal fluid may be pulled into the system, mixed with a drug or enzyme that is already in the drug and filter reservoir to extract harmful substances from the CSF, and passed through the filter back into CSF space while the drug or enzyme with extracted substances remains in the drug and filter reservoir. Thus, the drug or enzyme never enters the patient's CSF space. Periodically the drug and filter reservoir may be accessed, with a needle through the patient's skin for example, to remove substances filtered from the cerebrospinal fluid and to re-charge the reservoir with another medicinal dose.

Figure 4:
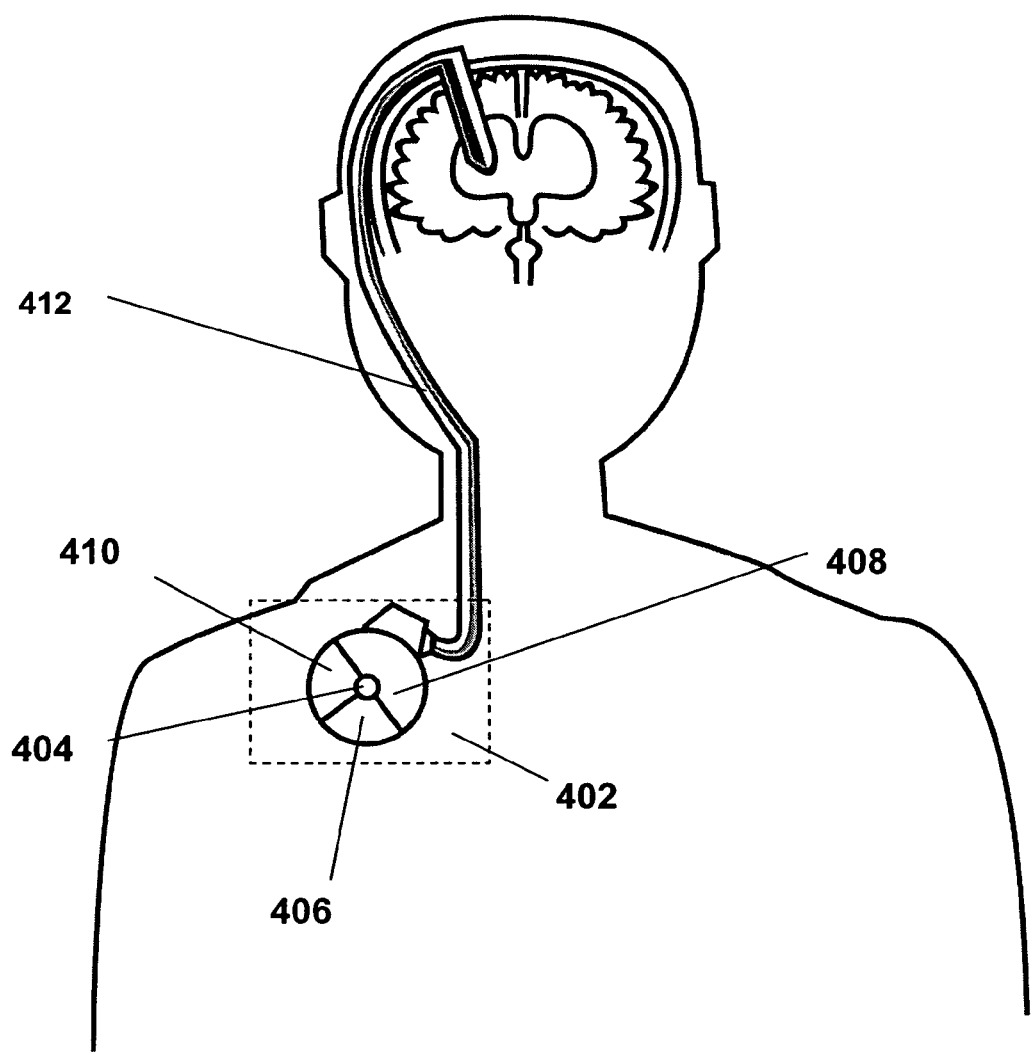
FIG. 4 is another drawing of a pump and filter for filtering cerebrospinal fluid, which depicts certain aspects of various embodiments of the present invention.

FIG. 4 is a drawing of another pump and filter system which may be employed in removing harmful organic anions and proteins from a mammalian's ventricular cerebrospinal fluid in accordance with embodiments of the present invention. The system depicted in FIG. 4 functions in the same manner as the system depicted in FIG. 3. However, whereas dual lumen catheter 304 is in fluid contact with a patient's spinal subarachnoid space, dual lumen catheter 412 is, instead, in fluid contact with the lateral ventricle of a patient's brain. Therefore, in an embodiment of the present invention implemented according to FIG. 4, cerebrospinal fluid would be extracted from the lateral ventricle of the patient's brain, processed by the pump and filter system, and returned back to the lateral ventricle of the patient's brain.

As shown, pump and filter system 402 comprises a dual lumen catheter 412 in fluid contact with drug and filter reservoir 408. Dual lumen catheter 412 is also in fluid contact with the lateral ventricle of a patient's brain. The pump and filter system further comprises a power supply 406, a drug port 404, and a pump 410. The drug and filter reservoir, drug port, and the pump are in fluid communication with each other. Therefore, the pump and filter system is in fluid communication with the lateral ventricle of the patient's brain.

Figure 5:
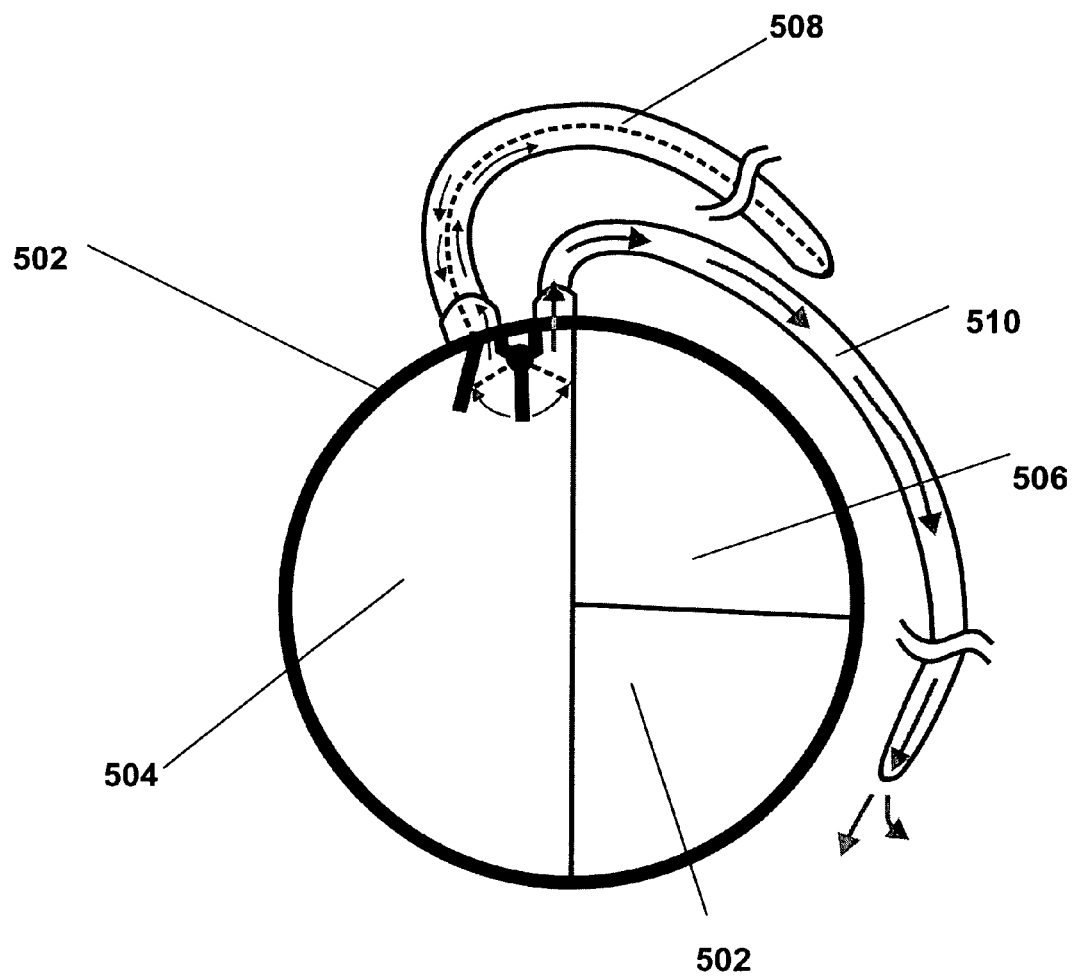
FIG. 5 is yet another drawing of a pump and filter for filtering cerebrospinal fluid, which depicts certain aspects of various embodiments of the present invention.

FIG. 5 is yet another drawing of a pump and filter, for filtering cerebrospinal fluid. The pump and filter system depicted in FIG. 5 functions in much the same manner and the pump and filter systems depicted in FIG. 3 and in FIG. 4. However, pump and filter system 500 incorporates a CSF diversion catheter 510 that may be used to implement a cerebrospinal fluid diversion feature according to still other embodiments of the present invention. With the feature, an externally programmable amount of filtered or unfiltered cerebrospinal fluid may be diverted from the pump and filter system to a different location in the body (e.g., the peritoneal cavity) to be re-absorbed.

Pump and filter system 500 comprises a pump 502, a drug or enzyme reservoir 504, a power supply 506, a dual lumen catheter 508, and CSF diversion catheter 510. Diversion catheter 510 allows the diversion of a programmed amount of filtered or un-filtered cerebrospinal fluid to be diverted to another part of the body (other then the lateral ventricle or the spinal subarachnoid space) to be re-absorbed. An externally programmable controller may be used to program a one-time bolus of a prescribed amount of cerebrospinal fluid to another location in the patient's body. Alternately, the pump and filter system may be programmed to send a slow continuous flow rate of cerebrospinal fluid to another location in the patient's body via the CSF diversion catheter. In diverting cerebrospinal fluid in said manner, the delicate balance between the production and absorption of cerebrospinal fluid in the CSF system may be maintained.

While the foregoing is directed to embodiments of the present invention, other and further embodiments of the invention may be devised without departing from the basic scope thereof, and the scope thereof is determined by the claims that follow.

The invention claimed is:

1. A method for removing harmful organic anions and proteins from a mammalian's ventricular cerebrospinal fluid comprising:
   a. implanting a pump and filter system comprising,
      i. a power supply compartment
      ii. an access port for injecting a medicinal dose and for removing filtered material
      iii. drug reservoir and
      iv. pump with filter, wherein the access port, the drug reservoir and the pump and filter system are in fluid communication
   b. implanting a dual lumen catheter in fluid contact with the pump and filter system and in fluid contact with the spine's sub-arachnoid space
   c. supplying a medicinal dose into the drug reservoir via the access port
   d. extracting cerebrospinal fluid from the sub-arachnoid space into the drug reservoir via a first lumen of the catheter
   e. delivering the cerebrospinal fluid through the filter back into the sub-arachnoid space via a second lumen of the catheter
   f. removing filtered material from the pump and filter system via the access port, and
   g. supplying another medicinal dose into the drug reservoir via the access port when another medicinal dose is required.

2. The method of claim 1 wherein the medicinal dose is a drug that attracts harmful proteins like A-Beta and Tau.

3. The method of claim 2 wherein the drug is Alzhemed™.

4. The method of claim 1 wherein the medicinal dose is an enzyme capable of digesting A-Beta or other harmful proteins.

5. The method of claim 1 further comprising implanting a diversion catheter in fluid contact with the pump and filter system to divert cerebrospinal fluid to another part of the body and wherein the pump and filter system is externally programmable for at least
   h. controlling the rate of filtering cerebrospinal fluid
   i. setting a one-time bolus of an amount of cerebrospinal fluid to be diverted to another location of the body to be re-absorbed or
   j. setting a slow continuous rate of diverting cerebrospinal fluid to another location of the body to be re-absorbed.

6. The method of claim 5 wherein another part of body is the peritoneal cavity.

7. The method of claim 5 where in another part of the body is the right atrium of the heart.

* * * * *